United States Patent [19]

Bertelli

[11] 4,011,317
[45] Mar. 8, 1977

[54] STEROID DERIVATIVES

[75] Inventor: Aldo Bertelli, Milan, Italy

[73] Assignee: Rorer Italiana S.p.A., Milan, Italy

[22] Filed: Aug. 22, 1975

[21] Appl. No.: 607,042

[52] U.S. Cl. .......................... 424/243; 260/397.45
[51] Int. Cl.² ......................................... A61K 31/56
[58] Field of Search ............... 260/397.45; 424/243

[56] References Cited

FOREIGN PATENTS OR APPLICATIONS

| | | | |
|---|---|---|---|
| 1,223,087 | 2/1971 | United Kingdom | 260/397.45 |
| 965,935 | 8/1964 | United Kingdom | 260/397.45 |

Primary Examiner—Elbert L. Roberts
Attorney, Agent, or Firm—Young & Thompson

[57] ABSTRACT

The present invention is concerned with new derivatives of the cortisone series having in particular a cortisonelike action of the steroid anti-inflammatory type.

The compounds of the present invention are represented by the general formula:

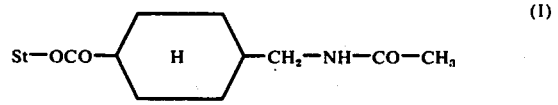

(I)

in which:

St is a steroid group of the pregnane, pregnene, or pregnadiene series, the ester linkage being at position 21 of the steroid group.

5 Claims, No Drawings

STEROID DERIVATIVES

The present invention is concerned with new derivatives of the cortisone series having in particular a cortisonelike action of the steroid anti-inflammatory type, a process for their preparation and their therapeutic applications.

The compounds of the present invention are represented by the general formula:

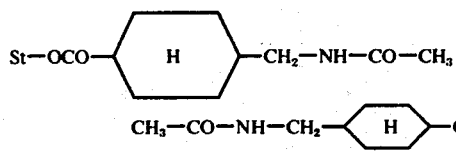

(I)

in which:

St is a steroid group of the pregnane, pregnene, or pregnadiene series, the ester linkage being at position 21 of the steroid group.

The invention also provides a process for the preparation of compounds of formula (I) in which the steroid is reacted with the acid chloride of 4-N-acetylaminomethylcyclohexanecarboxylic acid in a suitable organic solvent (for example chloroform or benzene), in the presence of a hydrochloric acid acceptor (for example pyridine).

Suitable base steroids are, for example, prednisolone, triamcinolone, betamethasone, chlorcortolone and fluocortolone.

The following non-limitative examples illustrate the preparation of compounds according to the invention.

EXAMPLE 1

Preparation of prednisolone 21-(4-N-acetylaminomethylcyclohexanecarboxylate)

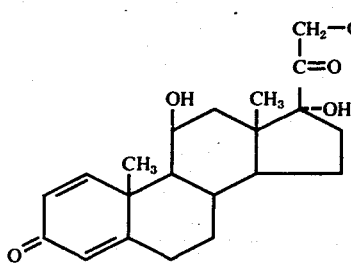

a. Preparation of 4-N-acetylaminomethylcyclohexanecarboxylic acid:

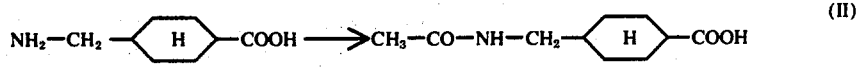

(II)

20 grams of aminomethylcyclohexanecarboxylic acid dissolved in 100 cm$^3$ of anhydrous pyridine were cooled to 0° to 5° C. 15 cm$^3$ of acetic anhydride were added to this solution with stirring without exceeding 10° C. When the addition was finished, the mixture was allowed to stand for 12 hours, then the solvent was evaporated off under vacuum and the residue was taken up in a solution of sodium bicarbonate. The residue was filtered, then crystallized in water. Melting point 130° C.

b. Preparation of the acid chloride of 4-N-acetylaminomethylcyclohexanecarboxylic acid:

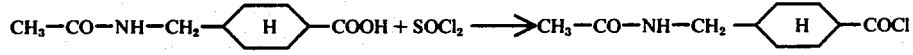

(III)

2 grams of the acid (II) were suspended in 10 cm$^3$ of anhydrous benzene and treated, under agitation, with 2 grams of thionyl chloride. After 60 minutes, the solution was contacted with petroleum ether to complete precipitation and then filtered rapidly. 2 grams of the acid chloride were obtained.

c. Preparation of prednisolone ester:

1 g of prednisolone was dissolved in 10 cm$^3$ of a solution obtained by dissolving 0.8 grams of the acid chloride (III) in anhydrous chloroform free of ethanol. The mixture was allowed to stand for 48 hours, and the solvent was evaporated off under vacuum. An oil was obtained which became solid on treatment with a saturated bicarbonate solution. The desired ester was obtained by crystallization from ethanol.

Melting point 246° C; Molecular weight 541; Empirical formula $C_{31}H_{43}O_7N$; C = 69.51%; H = 6.96%; N = 2.61%.

The identity of the product was confirmed by elementary analysis, infra-red and NMR spectra, qualitative tests for detection of prednisolone, and by spectrophotometric comparison of prednisolone, 4-N-acetyl-aminomethylcyclohexanecarboxylic acid and the reaction product.

EXAMPLE 2

Preparation of triamcinolone 21-(4-N-acetyl-aminomethylcyclohexanecarboxylate)

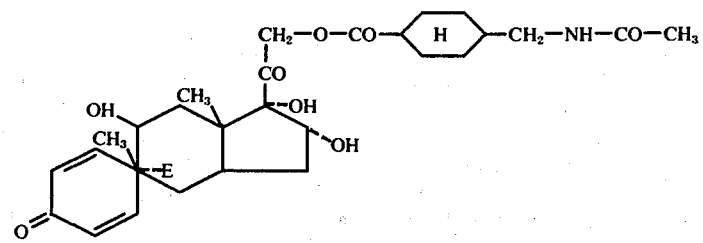

1 gram of triamcinolone was dissolved in 10 cm³ of anhydrous pyridine. This solution was poured into 10 cm³ of a solution obtained by dissolving 0.8 grams of the acid chloride (III) of Example 1 in anhydrous chloroform. The mixture was allowed to stand for 48 hours, then the solvent was evaporated off under vacuum. A solid product was obtained which was crystallized from ethanol.

Melting point 203° C; yield 80%; Molecular weight 575.5; Empirical formula $C_{31}H_{42}FNO_8$.

The identity of the product was confirmed by elementary analysis, infra-red and NMR spectra, qualitative tests for detection of triamcinolone and by spectrophotometric comparison of triamcinolene, 4-N-acetyl aminomethylcyclohexanecarboxylic acid and the reaction product.

The new compounds, while conserving the typical activity of cortisonic substances, show more advantageous pharmacological and therapeutic properties. In particular, they have a more intense and prolonged activity, which may be achieved equally by topical, dermal application or using an aerosol.

Accordingly the invention also provides a therapeutic composition containing as active principle a compound of formula (I).

The active principle is generally in admixture with a therapeutically administrable vehicle or excipient.

For the purposes of illustration, results of a toxicological and pharmacological study are given, which were based on prednisolone 21-(4-N-acetyl-aminomethylcyclohexanecarboxylate) as a representative example of the compounds of formula (I).

Toxicological Tests

In common with other derivatives of cortisone, the new product has no significant toxicity, whether it is administered orally, parenterally, rectally or topically. It has the advantage, when compared with cortisone, that it has less effect on the calcium or protein metabolism. If the starting molecules are considered, it is seen that there are no modifications in the elimination of potassium, sodium or water.

Compared to the base steroid, the new product influences with less intensity the experimental formation of gastric ulcers (by the method of Schay, by constriction, and by glucose).

Pharmacological Tests a. Test for cortisonelike activity

What characterizes the new product in comparison to the base steroid, is a more prolonged corticoidal activity and a more powerful local action, whether dermal or bronchial.

The tests carried out (evaluation of the reduction of hematic corticosterone caused by inhibition of the hypophysis-suprarenal axis, an evaluation which can be considered parallel to the activity) confirms the prolonged action of the product.

Indeed, after having administered 4 mg/kg of prednisolone, the level of plasmatic corticosterone returns to its initial values (30 mcg/100 cm³) after 18 hours, while after having administered equimolar quantities of prednisolone 21-(4-N-acetyl-aminomethylcyclohexanecarboxylate), the corticoidal activity, after an identical period of time, was found to be still very high. (The levels are around 18 mcg/100 cm³ of plasma.)

b. Anti-phlogistic activity

A comparison made between equimolar doses of prednisolone and the new product showed, according to various tests made, a more intense anti-phlogistic action for the new product.

The tests carried out were on local oedemas of rat paws caused by carragheenin, dextran and serotonine. In the case of carragheenin-induced oedema, the administration of prednisolone at a dose of 4 mg/kg caused hardly any effect, while administration of the same dose with the new product completely prevented its formation.

The same result was obtained more interestingly on experimental tests on granuloma of deer. The granuloma was reduced by half on administration of 4 mg/kg of the new product, and its effect was nearly double that of prednisolone at the same dosage.

c. Tests for anti-anaphylactic activity

By these tests it was possible to observe that bronchospasm and anaphylactic shock, induced by a heterogenous serum in sensitized guinea pigs, were blocked more readily by the new product than by prednisolone. It was equally possible to demonstrate a more favourable activity by tests on cutaneous oedema caused in rats by intradermal injection of an immunoserum. (It was possible to obtain inhibition of the oedema by administering 2 mg/kg of the new product, against 5 mg/kg of prednisolone.) With regard to diffusion under the skin of rats of dyestuff (Evans Blue) induced by injection of serotonine or histamine, the topical application of the new product prevented this more effectively and for a longer time than a similar application of prednisolone.

The tests carried out indicated that the new compounds of the present invention can be used more advantageously than the base steroid in human therapeutic treatment for all conditions responsive to steroids.

The pharmaceutical composition can be administered orally, parenterally, rectally, topically or by aerosol, in the form of tablets, pills, syrups, ampoules, powders, ointments, creams or lotions, the active ingredients being in admixture with appropriate vehicles or excipients.

Several non-limitative examples of pharmacological formulations of the compounds of the present invention are given below:

tablets containing 2 to 10 mg of active ingredient, injectable ampoules containing 10 to 30 mg of active ingredient, suppositories containing 5 to 20 mg of active ingredient, ointments, lotions, solutions for aerosols, containing 0.05 to 2% of active ingredient.

The dose administerable each 24 hours varies according to the therapeutic requirements.

Having now described my invention what I claim as new and desire to secure by Letters Patent is:

1. 11β,17,21-trihydroxypregna-1,4-diene-3,20-dione 21-(4-N-acetyl-aminomethylcyclohexanecarboxylate).

2. 9-fluoro-11β,16α,17,21-tetrahydroxypregna-1,4-diene-3,20-dione 21-(4-N-acetyl-aminomethylcyclohexanecarboxylate).

3. A compound of the formula:

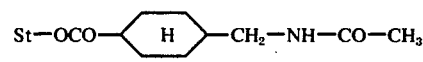

in which:

St represents a radical selected from 11β,17,21-trihydroxypregna-1,4-diene-3,20-dione; 9-fluoro-11β,16α,17,21-tetrahydroxy-pregna-1,4-diene-3,20-dione; 9-fluoro-11β,17,21-trihydroxy-16β-methylpregna-1,4-diene-3,20-dione; 6α-chloro-11β,21-dihydroxy-16α-methylpregna-1,4-diene-3,20-dione; and 6α-fluoro-11β,21-dihydroxy-16α-methylpregna-1,4-diene-3,20-dione.

4. A therapeutic composition having corticoidal, anti-phlogistic and anti-anaphylactic activity comprising a compound of the formula:

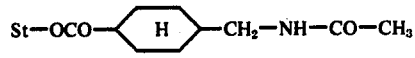

in which:
St represents a radical selected from 11β,17,21-trihydroxypregna-1,4-diene-3,20-dione; 9-fluoro-11β,16α,17,21-tetrahydroxy-pregna-1,4-diene-3,20-dione; 9-fluoro-11β,17,21-trihydroxy-16β-methylpregna-1,4-diene-3,20-dione; 6α-chloro-11β,21-dihydroxy-16α-methylpregna-1,4-diene-3,20-dione; and 6α-fluoro-11β,21-dihydroxy-16α-methylpregna-1,4-diene-3,20-dione; in admixture with a therapeutically acceptable vehicle.

5. A composition according to claim 4, in unit dosage form.

* * * * *